United States Patent [19]

Dormoy et al.

[11] Patent Number: 4,625,033

[45] Date of Patent: Nov. 25, 1986

[54] PROCESS FOR PREPARING 5-AZA-INDOLE AND INTERMEDIATES USED IN THIS PROCESS

[75] Inventors: Jean-Robert Dormoy; Alain Heymes, both of Sisteron, France

[73] Assignee: Sanofi, Paris, France

[21] Appl. No.: 738,438

[22] Filed: May 28, 1985

[30] Foreign Application Priority Data

May 25, 1984 [FR] France ............................ 84 08275

[51] Int. Cl.$^4$ .................. C07D 471/04; C07D 213/38
[52] U.S. Cl. .................................. 546/113; 546/329; 546/193; 546/281; 546/312; 544/124
[58] Field of Search ............... 546/275, 113, 304, 329, 546/193, 281, 312; 544/124

[56] References Cited

PUBLICATIONS

Journal of Medicinal Chemistry, vol. 14, No. 11, Nov. 1972, pp. 1168-1171, Washington, D.C.
Chemical Abstracts, vol. 87, No. 25, Dec. 19, 1977, p. 714, "Synthesis of 6-Azaindole".
Khim. Geterotsikl. Soedin., 1977, (8), 1135-6.
Synthesis of 4-Azaindoles, Azimov et al.

Primary Examiner—Henry R. Jiles
Assistant Examiner—J. Richter
Attorney, Agent, or Firm—Bacon & Thomas

[57] ABSTRACT

A process for preparing 1H-pyrrolo-[3,2-c]-pyridine or 5-aza-indole in high yield, comprising condensing 3-methyl-4-nitropyridine-1-oxide with a compound having a formula

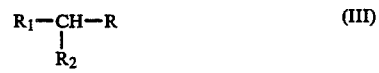

wherein R represents a di-loweralkylamino, morpholino, piperidino or pyrrolidino group and $R_1$ and $R_2$, which are the same or different, each represent a loweralkoxy group or a group R as defined; to form an enamine having a formula:

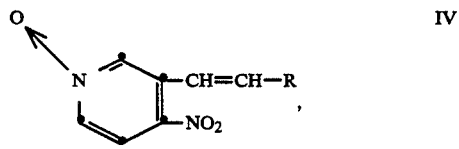

wherein R is as define and subjecting the enamine IV to reduction cyclization; the enamines IV are new compounds.

17 Claims, No Drawings

PROCESS FOR PREPARING 5-AZA-INDOLE AND INTERMEDIATES USED IN THIS PROCESS

This invention relates to a novel process for preparing a pyridine derivative and to intermediates used in this process.

In particular, the invention concerns a novel process for preparing 1H-pyrrolo-[3,2-c]-pyridine or 5-aza-indole of formula:

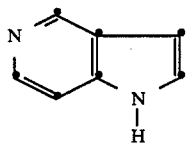

I

This compound is particularly valuable as an intermediate for the synthesis iof biologically active compounds, for instance for the preparation of the anti-inflammatory compounds 4-amino-aryl-5-aza-indole described in Chimie Therapeutique, 5, 559–566 (1973).

The processes described in the chemical literature for preparing 5-aza-indole are essentially useful for laboratory purposes and difficult to carry out on the industrial plane. For example, a method for preparing this compound is described in Am. Chem., 612, 153–157 (1958) involving the photochemical reduction of the naphthyridine ring. Such a photochemical reduction step is difficult to apply when large amounts of product are involved.

Furthermore, the total yields in 5-aza-indole is only 11%.

Moreover, there is described in J. Org. Chem. 30, 2531–2533 (1965) another process for preparing 5-aza-indole from 3-methyl-4-amino-pyridine.

This process would appear to be the most effective one reported in the literature.

However, no other research workers have succeeded in obtaining either the overall yield of 36% or, more particularly, that of the final step nor was it found possible to reproduce these results during the development of the present invention.

Other processes have also been proposed, for instance in Tetrahedron Letters, 24, 1909–1912 (1969) but these appear to be of little value since the starting products used are difficult to obtain.

As a result, it became imperative to find an industrial process for preparing 5-aza-indole which would obviate the disadvantages of the processes hitherto described.

YAKONTOV et al. have described in Khim. Geterotsikl. Soedin, 10, 1425 (1977) (CA 88, 37665p) the preparation of 4-aza-indole and in Khim. Geterotsikl. Soedin, 8, 1135–1136 (1977) (CA 87, 201382w) the preparation of 6-aza-indole involving, in a first step, the production of an enamine.

Following this method, 4-aza- and 6-aza-indoles are obtained from 2-methyl-3-nitro-pyridine and 4-methyl-3-nitro-pyridine respectively.

These pyridine derivatives are condensed with formamide acetal to form the corresponding O-nitro-β-dimethylaminovinyl-pyridine which is then reduced on palladium catalyst to provide the corresponding aza-indole.

The yields reported for each of these aza-indoles are in the range of 80 to 100% calculated from the methylpyridine derivative.

In view of the structural similarity between 5-aza-indole on the one hand and 4-aza- and 6-aza-indoles on the other, attempts were made, when developing the present invention, to apply the above-described process to 3-methyl-4-nitro-pyridine, with a view to finally obtaining 5-aza-indole.

However, the total yields so obtained were found to be relatively low, being about 50% calculated from the methyl-pyridine derivative.

It would appear, therefore, that no industrially viable process for preparing 5-aza-indole can be obtained by merely applying the prior art procedures.

Consequently, it was essential to find an industrial process for preparing 5-aza-indole which was simple to operate and gave high yields at the lowest possible cost.

It has now been found, in accordance with the present invention, that 5-aza-indole can be obtained by using 3-methyl-4-nitro-pyridine-1-oxide as the starting methyl-pyridine derivative to form an enamine which is subsequently converted to the desired aza-indole.

This discovery is moreover surprising in the light of Chem. Ber., 101, 4048–4056 (1958) which clearly suggests the use of a non oxidated methyl-pyridine to form an enamine rather than the use of the corresponding methyl-pyridine N-oxide derivative.

For example, it is reported therein that 4-(2-dimethylamino-vinyl)-pyridine was obtained, in a yield of 84%, from 4-methyl-pyridine and a formamide acetal while 4-(2-dimethylamino-vinyl)-pyridine-N-oxide was produced in a yield of only 18% from 4-methyl-pyridine-N-oxide.

Thus, a first object of the invention relates to a process for preparing 5-aza-indole, whereby 3-methyl-4-nitro-pyridine-1-oxide of formula:

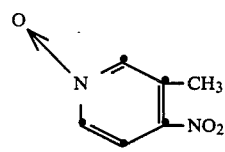

II is condensed at a temperature between 0° and 200° C. usually between 100° and 150° C. with a compound of general formula:

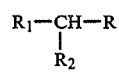

III in which R represents a dimethylamino, diethylamino, dipropylamino, dibutylamino, morpholino, piperidino or pyrrolidino group and $R_1$ and $R_2$, which are the same or different, each represent a methoxy, ethoxy or propoxy group or a group R as hereabove defined, to obtain a enamine of general formula:

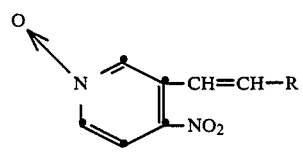

IV in which R has the same meaning as above and further submitting the enamine, in a solvent, to a reduction cyclisation with hydrogen in the presence of a catalyst such as, for example, Raney's nickel or palladium charcoal, to provide the desired 5-aza-indole.

Another object of the invention relates to the enamines of formula IV as industrial products for preparing 5-aza-indole in accordance with the aforesaid process.

The enamines in question are formed in the absence of solvent or preferably in an appropriate solvent such as N,N-dimethylformamide or a lower alcohol such as methanol or ethanol.

The reduction cyclisation is performed in a lower alcohol, for instance ethanol, in a glycol, in acetic acid or in N,N-dimethylformamide at a temperature between 0° and 120° C. usually at a temperature of about 60° C.

In accordance with the process of the invention as described, 5-aza-indole can be obtained in yields of about 80% calculated from the compound of formula II.

Taken as a whole, the process of the invention is more simple and more productive than the method suggested by YAKONTOV et al.

The application of the YAKONTOV et al. process for synthetizing 3-methyl-4-nitro-pyridine would, in fact, require the preparation of 3-methyl-4-nitro-pyridine. This compound is usually obtained from 3-methyl-4-nitro-pyridine-1-oxide, which is the compound of formula II above, by reduction with, for instance, phosphorous trichloride.

The process of the invention avoids this intermediate reduction step, the N-oxide group of the compound of formula II being reduced during the final reduction cyclisation.

Within the framework of the invention, a comparison was made between two processes, each starting from 3-methyl-4-nitro-pyridine-1-oxide, of which one was in accordance with the operating conditions of the invention and the other with a procedure similar to that of YAKONTOV et al. i.e. involving a transitory step of reduction of this N-oxide compound to 3-methyl-4-nitro-pyridine.

In the first case, the yield in 5-aza-indole was found to be about 80% and in the second the yield was only 44%.

Therefore, the overall process of the invention appears to be of greater economic value than the process suggested by the prior art.

Moreover, in accordance with a particular mode of applying the process of the invention, in which an addition product (referred to hereunder as an "adduct") resulting from the reaction of morpholine and methyl or ethyl orthoformiate is used, the step of preparing the enamine of formula IV is carried out in the medium where the adduct is formed.

For this purpose, an appropriarte stoichiometric relationship between reagents is used, generally a molar ratio of 3 to 9/1.5 to 4.5, preferably a molar ratio of 6/3 in morpholine/alkyl orthoformate per mol of 3-methyl-4-nitro-pyridine-1-oxide, to obtain overall yields of at least 70% in 5-aza-indole.

The use of such a morpholine/alkyl orthoformate adduct also offers appreciable advantages which render the procedure preferable.

The other compounds of formula III which are previously isolated, such as the dimethyl or diethyl acetals of N,N-dimethylformamide do, in fact, require a two-step synthesis namely the chlorination of N,N-dimethylformamide followed by the etherification with sodium methylate or ethylate, and then final distillation.

The production of enamine from these acetals is thus carried out following a three-step process.

As against this, the preferred procedure in accordance with the invention necessitates two chemical steps in the same reaction medium without isolating or purifying the intermediate morpholine/alkyl orthoformate adduct resulting from the first chemical step. This procedure is not described by YAKONTOV et al. in the above-cited references in which previously isolated formamide acetals are used.

In addition, the adduct in question may be preferred to trismorpholinomethane, another compound of formula III which is not easy to store in view of its hygroscopicity.

Thus, the preferred procedure of the invention enables yields in 5-aza-indole to be obtained which are similar to those produced from previously isolated compounds of formula III, but, the procedure of the invention is less complicated and of greater economic value.

The compounds of formula III above, for instance N,N-dimethylformamide dimethylacetal, N,N-dimethylformamide diethylacetal and trismorpholinomethane are known compounds or compounds which can be prepared using known methods such as those described in Angew. Chem. 72, 836–845 (1960), Helv. Chim. Acta, 44 (5), 1203–1211 (1961) or in European Patent Application No. 001633.

As regards 3-methyl-4-nitro-pyridine-1-oxide of formula II, this can be obtained by nitrating 3-methyl-pyridine-1-oxide itself prepared by oxidating 3-methyl-pyridine.

The non-limitative Examples, which follow, illustrate the invention:

EXAMPLE 1

Preparation of 1H-pyrrolo-[3,2-c]-pyridine or 5-aza-indole (a) 3-($\beta$-Dimethylaminovinyl)-4-nitro-pyridine-1-oxide In 10 ml of N,N-dimethylformamide, were dissolved 77 g (0.5 mol) of 3-methyl-4-nitro-pyridine-1-oxide and 80 ml (0.6 mol) of N,N-dimethylformamide dimethylacetal.

The medium was placed under a dry flow of nitrogen and, while stirring progressively heated to 120° C. Heating was maintained for 2 to 3 hours at 120° C. causing distillation of the methanol produced by the reaction. The methanol, N,N-dimethylformamide dimethylacetal and N,N-dimethylformamide were eliminated under reduced pressure (60° C., 4 mmHg). The brown-red residual solid was taken up in ethanol and the fraction re-dissolved by adding ethyl ether was precipitated.

The crystals so obtained were suction-filtered, washed with ethyl ether and dried under vacuum.

In this manner, 99 g of 3-($\beta$-dimethylaminovinyl)-4-nitro-pyridine-1-oxide were obtained in the form of violet-brown crystals.

Yield: 95%.

M.P.: 213°–214° C.

| Elementary analysis | C | H | N |
|---|---|---|---|
| Calculated % | 51.67 | 5.26 | 20.09 |
| Found % | 51.67 | 5.11 | 20.39 |

N.M.R. spectrum (CDCl$_3$/TMS): 3.0 (s, 6H); 5.9 (d, 1H, J=13 Hz); 7.4 (d, 1H, J=13 Hz); 7.5–8.0 (m, 2H).

Coupling of 13 Hz indicates a trans stereochemistry of the bond of the enamine.

(b) 1H-Pyrrolo-[3,2-c]-pyridine

In a PARR apparatus, working at atmospheric pressure were placed 2.1 g (0.01 mol) of 3-(β-dimethylaminovinyl)-4-nitro-pyridine-1-oxide, 3.15 g of Raney's nickel (at 50% in water) and 25 ml of ethanol. The mixture was vigorously stirred at room-temperature for 14 h and then at 60° C. until absorption of hydrogen ceased.

The catalyst was suction-filtered on Celite (a commercially available diatomaceous product, the word Celite being a registered Trade Mark) and washed several times with ethanol. The ethanol solution was discoloured by means of active charcoal, concentrated under vacuum and rapidly filtered on silica. After evaporating the solvent, 0.98 g of 1H-pyrrolo-[3,2-c]-pyridine was obtained in the form of yellowish white crystals.

Yield: 84%.
M.P.: 110°–122° C.

EXAMPLE 2

Preparation of 5-aza-indole (a) 3-(β-N-Morpholinovinyl)-4-nitro-pyridine-1-oxide In 20 ml of N,N-dimethylformamide were dissolved 7.7 g (0.05 mol) of 3-methyl-4-nitro-pyridine-1-oxide and 16.3 g (0.06 mol) of trismorpholinomethane.

The medium was placed under a dry flow of nitrogen and heated to 100° C. This temperature was maintained for 2 h. When the N,N-dimethylformamide solution was cooled, a dark red product crystallized which was suction-filtered, washed with methanol and dried under vacuum.

In this manner, 11.55 g of 3-(β-N-morpholinovinyl)-4-nitro-pyridine-1-oxide were obtained.
Yield: 92%.
M.P.: 230° C.

(b) 5-Aza-indole

In a PARR apparatus, working at atmospheric pressure, were placed 2.5 g (0.010 mol) of 3-(β-N-morpholinovinyl)-4-nitro-pyridine-1-oxide, 3.15 g of Raneys's nickel (at 50% in water) and 25 ml of ethanol. The mixture was vigorously stirred at room-temperature for 15 h and then at 60° C. until absorption of hydrogen ceased.

The catalyst was suction-filtered on Celite and washed several times with ethanol. The ethanol solution was discoloured by means of active charcoal and concentrated under vacuum. After rapid filtration of the residue on silica, 1 g of 5-aza-indole was obtained in the form of yellow crystals.
Yield: 85%.
M.P.: 109°–110° C.

EXAMPLE 3

Preparation of 5-aza-indole (a) 3-(β-N-Morpholinovinyl)-4-nitro-pyridine-1-oxide In 5 ml of N,N-dimethylformamide were dissolved 8.9 g (0.06 mol) of ethyl orthoformate, 10.45 g (0.12 mol) of morpholine and 0.36 g (0.006 mol) of glacial acetic acid.

The medium was placed under dry nitrogen atmosphere and progressively heated to 140° C. for 45 min. until distillation of the methanol produced by the reaction ceased.

The mixture was cooled and then 3.08 g (0.02 mol) of 3-methyl-4-nitro-pyridine-1-oxide were introduced.

The medium was heated to 140° C. and maintained at this temperature for 90 min. After cooling, the reagent in excess was partially evaporated under reduced pressure. The dark red crystals so obtained were suction-filtered, washed with methanol and dried under vacuum.

In this manner, 4.2 g of 3-(β-N-morpholinovinyl)-4-nitro-pyridine-1-oxide were obtained.
Yield: 84%.
M.P.: 228° C.

(b) 5-Aza-indole

Following the same procedure as that described in Example 2b, 5-aza-indole was obtained in a yield of 85%.

We claim:

1. Process for preparing 1H-pyrrolo-[3,2-c]-pyridine or 5-aza-indole of formula:

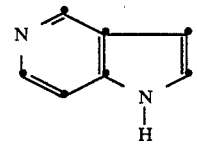

I whereby 3-methy-4-nitro-pyridine-1-oxide of formula:

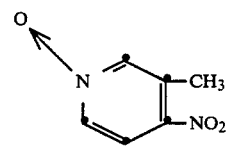

II is condensed, in a solvent or in the absence of a solvent, with a compound having a formula:

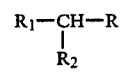

III wherein R represents a dimethylamino, diethylamino, dipropylamino, dibutylamino, morpholino, piperidino or pyrrolidino group and R$_1$ and R$_2$, which are the same or different, each represent a methoxy, ethoxy or propoxy group or a group R as defined above, to provide an enamine of general formula:

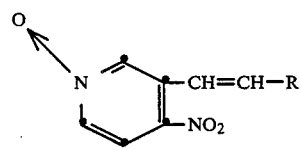

IV in which R has the same meaning as above which is then submitted in a solvent to reduction cyclisation with hydrogen in the presence of a catalyst to obtain the required 5-aza-indole.

2. A process according to claim 1, wherein the condensation is carried out at a temperature between 0° and 200° C. and the reduction cyclisation at a temperature between 0° and 120° C.

3. A process according to claim 2 wherein the condensation is carried out at a temperature between 100° and 150° C. and the reduction cyclisation at a temperature of about 60° C.

4. A process according to claim 1, wherein the condensation is carried out in N,N-dimethylformamide and the reduction cyclisation in ethanol as solvents.

5. A process according to claim 1, wherein the catalyst is Raney's nickel or palladium charcoal.

6. A process according to claim 1, wherein the compound of formula III is N,N-dimethylformamide dimethylacetal, N,N-dimethylformamide diethylacetal or trismorpholinomethane.

7. A process according to claim 1, wherein the compound of formula III is an adduct obtained by reacting morpholine with methyl or ethyl orthoformate, in a reaction medium and wherein said adduct is condensed with 3-methyl-4-nitro-pyridine-1-oxide in said reaction medium where the adduct was formed to provide the enamine of formula IV.

8. A process according to claim 7, wherein the adduct used is obtained by reacting 3 to 9 mols of morpholine with 1.5 to 4.5 moles of methyl or ethyl orthoformate per mol of 3-methyl-4-nitro-pyridine-1-oxide.

9. A process according to claim 7, wherein the adduct used is obtained by reacting 6 mols of morpholine with 3 mols of methyl or ethyl orthoformate per mol of 3-methyl-4-nitro-pyridine-1-oxide.

10. Enamines having a formula:

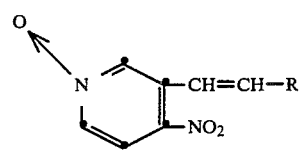

(IV)

in which R represents a dimethylamino, diethylamino, dipropylamino, dibutylamino, morpholino, piperidino or pyrrolidino group.

11. An enamine as claimed in claim 10 wherein R is a morpholino group.

12. A process according to claim 3, wherein the condensation is carried out in N,N-dimethylformamide and the reduction cyclisation in ethanol as solvents.

13. A process according to claim 12, wherein the catalyst is Raney's nickel or palladium charcoal.

14. A process according to claim 3, wherein the compound of formula III is N,N-dimethylformamide dimethylacetal, N,N-dimethylformamide diethylacetal or trismorpholinomethane.

15. A process according to claim 3, wherein the compound of formula III is an adduct obtained by reacting morpholine with methyl or ethyl orthoformate, in a reaction medium and wherein said adduct is condensed with 3-methyl-4-nitro-pyridine-1-oxide in said reaction medium where the adduct was formed to provide the enamine of formula IV.

16. A process according to claim 15, wherein the adduct used is obtained by reacting 3 to 9 mols of morpholine with 1.5 to 4.5 moles of methyl or ethyl orthoformate per mol of 3-methyl-4-nitro-pyridine-1-oxide.

17. A process according to claim 15, wherein the adduct used is obtained by reacting 6 mols of morpholine with 3 mols of methyl or ethyl orthoformate per mol of 3-methyl-4-nitro-pyridine-1-oxide.

* * * * *